US008252313B2

(12) United States Patent
Wedekind et al.

(10) Patent No.: US 8,252,313 B2
(45) Date of Patent: *Aug. 28, 2012

(54) METHODS FOR DIETARY MANAGEMENT OF CATS WITH HYPERTHYROIDISM

(75) Inventors: Karen Wedekind, Meriden, KS (US); Claudia Kirk, Louisville, TN (US); Raymond Nachreiner, E. Lansing, MI (US); Timothy VandeGiessen, Topeka, KS (US); Kim Gene Friesen, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 998 days.

This patent is subject to a terminal disclaimer.

(21) Appl. No.: 10/871,991

(22) Filed: Jun. 18, 2004

(65) Prior Publication Data

US 2005/0058691 A1 Mar. 17, 2005

Related U.S. Application Data

(60) Provisional application No. 60/480,152, filed on Jun. 20, 2003.

(51) Int. Cl.
*A23K 1/17* (2006.01)
*A61K 38/00* (2006.01)

(52) U.S. Cl. .................... 424/442; 514/2.1
(58) Field of Classification Search ............... None
See application file for complete search history.

(56) References Cited

U.S. PATENT DOCUMENTS

| 5,017,389 | A | 5/1991 | Green |
| 5,084,482 | A | 1/1992 | Hirsch et al. |
| 5,484,623 | A * | 1/1996 | McLean ................. 426/601 |
| 5,885,592 | A | 3/1999 | Duan et al. |
| 6,046,308 | A | 4/2000 | Glücksmann |
| 6,071,415 | A | 6/2000 | Frommer et al. |
| 6,245,364 | B1 * | 6/2001 | Jones et al. ................. 426/2 |
| 2003/0077254 | A1 * | 4/2003 | Ramaekers ............... 424/93.3 |

FOREIGN PATENT DOCUMENTS

| WO | WO 01/17364 | * | 3/2001 |
| WO | WO 0117364 A1 | * | 3/2001 |
| WO | WO 03/039562 | | 5/2003 |
| WO | WO 2004/112499 | | 12/2004 |
| WO | WO 2007/087623 | | 8/2007 |
| WO | WO 2007/133726 | | 11/2007 |
| WO | WO 2008/005980 | | 1/2008 |

OTHER PUBLICATIONS (Pathologic Basis of Disease by Robbins, Cotran and Kumar, third edition, pp. 1203-1204).*
Dietary Iodine Level and Thyroid Function in the Cat, Michael F. Tarttelin et al. American Institute of Nutrition. J. Nutr. 124:2477S-2578S, 1994.*
Michael et al. (Dietary Iodine Level and Thyroid Function in Cat: American Institute of nutrition. J. Nutr. 124: 2577S-2578S, 1994).*
Anonymous, "Royal Canin Veterinary Diet", Internet article cited in PCT/US2004/019853 as being retrieved from the internet on Oct. 15, 2004 (XP002301316); http://www.walthamusa.com/Learning%20Center/pf/LP21.pdf, pp. 6-8.
Anonymous, "Sodium selenate", Life Link, Internet article cited in PCT/US2004/019853 as being retrieved from the internet on Oct. 13, 2004 (XP002301317); http://www.lifelinknet.com/siteResources/ProductPages/Sodium-Selenate.asp.
Association of American Feed Control Officials (AAFCO), "AAFCO Cat Food Nutrient Profiles Based on Dry Matter," Official Publication, pp. 132-133 (2002).
Association of American Feed Control Officials (AAFCO), "AAFCO Cat Food Nutrient Profiles Based on Dry Matter," Official Publication, pp. 134-135 (2004).
Brewer, "Nutrition of the cat", J. Am. Vet. Med. Assoc., 180(10):1179-1182 (1982).
Brown et al., "Thyroid Growth Immunoglobulins in Feline Hyperthyroidism", Thyroid, 2(2):125-130 (1992).
Buffington, "Nutritional Requirements and Feeding Recommendations", The Cat: Diseases and Clinical Management 2nd Ed., pp. 133-151 (1994).
Court et al., "Identification and concentration of soy isoflavones in commercial cat foods", Am. J. Vet. Res., 63(2): 181-185 (2002).
Divi et al., "Anti-Thyroid Isoflavones from Soybean—Isolation, Characterization, and Mechanisms of Action", Biochemical Pharmacology, 54:1087-1096 (1997).
Doerge et al., "Goitrogenic and Estrogenic Activity of Soy Isoflavones", Environmental Health Perspectives, 110(3):349-353 (Jun. 2002).
Edinboro et al., "Epidemiologic study of relationships between consumption of commercial canned food and risk of hyperthyroidism in cats", JAVMA, 224(6):879-886 (Mar. 2004).
Ferguson, "Update on Diagnosis of Canine Hypothyroidism", Vet. Clin. N. Am. Small Anim. Pract., 24(3):515-539 (1994).
Foster et al., "Selenium status of cats in four regions of the world and comparison with reported incidence of hyperthyroidism in cats in those regions", Am. J. Vet. Res., 62(6):934-937 (Jun. 2001).
Fradkin et al., "Iodine-induced Thyrotoxicosis", Medicine 62(1): 1-20 (1983).
Gerber et al., "Etiopathology of Feline Toxic Nodular Goiter", Vet. Clin. N. Am. Small Anim. Pract. Thyroid Disorders, 24(3): 541-565 (May 1994).
Holzworth et al., "Hyperthyroidism in the Cat: Ten cases", J. Am. Vet. Med. Assoc., 176(4): 345-353 (Feb. 1980).
International Search Report PCT/US2004/019852; PCT Search Authority.

(Continued)

Primary Examiner — Frederick Krass
Assistant Examiner — Snigdha Maewall
(74) Attorney, Agent, or Firm — Michael F. Morgan

(57) ABSTRACT

Dietary compositions and methods for restoring normal thyroid function in a feline having hyperthyroidism to a more nearly normal state are disclosed. The compositions and methods restrict the amount of iodine intake in the feline.

21 Claims, No Drawings

OTHER PUBLICATIONS

International Search Report PCT/US2004/019853; PCT Search Authority.

Johnson et al., "Iodine content of commercially-prepared cat foods", NZ Vet. J., 40:18-20 (1992).

Kass et al., "Evaluation of Environmental, Nutritional, and Host Factors in Cats with Hyperthyroidism", J. Vet. Intern. Med., 13:323-329 (1999).

Kyle et al., "Serum free thyroxine levels in cats maintained on diets relatively high or low in iodine", NZ Vet. J., 42:101-103 (1994).

Labuc et al., "Feline Hyperthyroidism—A Short Review", Aust. Vet Practit. 16(3):139-142 (Sep. 1986).

Laurberg et al., "Environmental Iodine Intake Affects the Type of Nonmalignant Thyroid Disease", Thyroid, 11:457-469 (Nov. 2001).

Laurberg et al., "High incidence of multinodular toxic goiter in the elderly population in low iodine intake area vs. high incidence of Graves' disease in the young in a high iodine intake area: comparative surveys of thyrotoxicosis epidemiology in East-Jutland Denmark and Iceland", J Internal Med., 229:415-420 (1991).

Martin et al., "Evaluation of dietary and environmental risk factors for hyperthyroidism in cats", J. Am. Vet. Med. Assoc., 217(6):853-856 (Sep. 2000).

Martins et al., "Natural course of iodine-induced thyrotoxicosis (Jodbasedow) in endemic goiter area: A 5 year follow-up", J. Endocrin. Invest., 12:239-244 (1989).

Mason et al., "Determination of Iodine in Urine, Using Epithermal Instrumental Neutron Activation Analysis (EINAA), at the University of Missouri Research Reactor (MURR)", J. Radioanalytical Nucl. Chem., 195(1):57-65 (1995).

Mumma et al., "Toxic and protective constituents in pet foods", Am. J. Vet. Res., 47(7):1633-1637 (Jul. 1986).

National Research Council, "No. 13:Nutrient Requirement of Cats Revised 1978", National Academy of Sciences, pp. 10, 18-21; 25-27 (1978).

Nichols et al., "Longitudinal study of iodine in market milk and infant formula via epiboron neutron activation analysis", J. Radioanalytical Nucl. Chem., 236(1-2):65-69 (1998).

Pennington, "A review of iodine toxicity reports", J. Am. Dietetic Assoc., 90(11):1571-1581 (1990).

Peterson et al., "Spontaneous Feline Hyperthyroidism" (Abstract), Program of the 62nd Annual Meeting of the Endocrine Society, No. 516, 203 (1980).

Peterson et al., "Spontaneous Hyperthyroidism in the Cat" (Abstract), Proceedings of the American College of Veterinary Internal Medicine, 108 (Jul. 1979).

Peterson, "Propylthiouracil in the Treatment of Feline Hyperthyroidism", J. Am. Vet. Med. Assoc., 179:485-487 (Sep. 1981).

Ranz et al., "Estimation of Iodine Status in Cats", Waltham International Symposium: Pet Nutrition Coming of Age ; 2002 American Society for Nutritional Science. J. Nutr. 132: 1751S-1753S, (2002).

Scarlett et al., "Feline Hyperthyroidism: A Descriptive and Case-Control Study", Preventive Vet. Med., 6:295-309 (1988).

Schrauzer, "Selenomethionine: A Review of Its Nutritional Significance, Metabolism and Toxicity", J. Nutr., 130:1653-1656 (2000).

Simcock et al., "The role of selenium in companion animal health and nutrition", Institute of Food, Nutrition and Human Health, Massey University, Palmerton North, New Zealand, pp. 511-520.

Smith, "Changes and challenges in feline nutrition", J. Am. Vet. Med. Assoc., 203(10):1395-1400 (Nov. 1993).

Son et al., "Lack of Effect of Soy Isoflavone on Thyroid Hperplasia in Rats Receiving an Iodine-deficient Diet", Jpn. J. Cancer Res. 92:103-108 (Feb. 2001).

Tarttelin et al., "Dietary Iodine Level and Thyroid Function in the Cat", Am. Inst. Nutr. J. Nutr., 124:2577S-2578S (1994).

Tarttelin et al., "Serum free thyroxine levels respond inversely to changes in level of dietary iodine in the domestic cat", NZ Vet. J., 40:66-68 (1992).

Trepanier et al., "Efficacy and safety of once versus twice daily administration of methimazole in cats with hyperthyroidism", J. Am Vet. Med. Assoc., 222(7):954-958 (Apr. 2003).

Wedekind et al, "Defining the Safe Lower and Upper Limit for Selenium (Se) in Adult Dogs" (Abstract), Annual Meeting of Professional Research Scientists on Experimental Biology, New Orleans, Louisiana, USA (Apr. 20-24, 2002).

Wedekind et al., " Current AAFCO and NRC Recommendations for Selenium (Se) Are Too Low for Kittens" (Abstract), FASEBJ 14(4):A295 (2000).

Wedekind et al., "Effect of Varying Selenium (Se) Intake on Thyroid Hormone Metabolism in Dogs" (Abstract), FASEBJ 15(5):A953 (2001).

Wedekind et al., "Bioavailability of Selenium in Petfood Ingredients" (Abstract), Annual Meeting of Professional Research Scientists on Experimental Biology, New Orleans, Louisiana, USA (Apr. 6-9, 1997).

Wedekind et al., "Determination of the selenium requirement in kittens", J. Anim. Physiol. Anim. Nutr., 87:315-323 (2003).

Wedekind et al., "Selenium in Pet Foods—Is Bioavailability an Issue?", Proceedings, Purina Nutrition Forum: Supplement to Compendium on Continuing Education for the practicing Veterinarian, 22(9A):17-22 (Sep. 2000).

Wedekind, "The selenium requirement of the puppy", J. Anim. Physiol Anim Nutr., 88:1-8 (2004).

Yang et al., "Endemic selenium intoxication of humans in China", Am. J. Clin. Nutr., 37(5):872-881 (May 1983).

Yang et al., "Studies of Safe Maximal Daily Dietary Se-Intake in a Seleniferous Area in China. Part II. Relation Between Se-Intake and the Manifestation of Clinical Signs and Certain Biochemical Alterations in Blood and Urine", J. Trace Elem. Electrolytes Health Dis., 3(3):123-130 (1989).

Committee on Animal Nutrition, National Research Council "Nutrient Requirements of Cats, Revised Edition, 1986" The National Academies Press (1986), p. 18.

Behrend, 1999, "Medical Therapy of Feline Hyperthyroidism," Compendium on Continuing Education for the Practicing Veterinarian 21(3):234-244.

Fox et al., 1999, "Electrocardiographic and Radiographic Changes in Cats Comparison of Population Evaluated During 1992-1993 vs. 1979-1982," 35(1):27-31 with Hyperthyroidism: J. Anim. Hosp. Assoc.

Hoffmann et al., 2003, "Transdermal Methimazole Treatment in Cats with Hyperthyroidism," J. Feline Med. Surg. 5(2):77-82.

Peterson et al., 1983, "Feline Hyperthyroidism: Pretreatment Clinical and Laboratory Evaluation of 131 Cases," J. Amer. Vet. Med. Assoc. 183(1):103-110.

Peterson et al., 1993, "Comparison of the Disposition of Carbimazole and Methimazole in Clinically Normal Cats," Res. Vet. Sci. 54(3):351-355.

Robbins et al., *Pathologic Basis of Disease*, 3rd ed., pp. 1203-1204, 1984.

Slater et al., 2001, "Long-Term Health and Predictors of Survival for Hyperthyroid Cats Treated with Iodine 131," J. Vet. Intern. Med. 15(1):47-51.

Trepanier et al., 2006, "Medical Management of Hyperthyroidism," Clinical Techniques in Small Animal Practice 21(1):22-28.

Yu et al., 2002, "A Low-Selenium Diet Increases Thyroxine and Decreases 3,5,3' Triiodothyronine in the Plasma of Kittens," J. Anim. Physiol. a. Anim. Nutr. 86:36-41.

\* cited by examiner

METHODS FOR DIETARY MANAGEMENT OF CATS WITH HYPERTHYROIDISM

CROSS REFERENCE TO RELATED APPLICATION

This application claims the benefit of U.S. Provisional Application No. 60/480,152 filed Jun. 20, 2003, which is incorporated in its entirety by reference.

FIELD

This application relates generally to the management of the adult feline with hyperthyroidism disease and, more particularly, to methods for restoring normal thyroid function in a feline having hyperthyroidism.

BACKGROUND

The treatment options currently available to treat cats with hyperthyroidism are chronic administration of anti-thyroid drugs, surgical removal of one or both of the thyroid glands, and use of radioactive iodine to destroy the glandular tissue. However, each of these interventions has limitations and side effects. Accordingly, an unfilled need exists for methods for managing a feline with hyperthyroidism that improve the quality and quantity of life of the animal.

SUMMARY

Accordingly, the inventors herein have succeeded in discovering that restricting iodine intake in felines having hyperthyroidism improves thyroid function thereby restoring thyroid function to a more nearly normal state.

Thus, in various embodiments, the present invention can involve a method for restoring thyroid function to a more nearly normal state in a feline having hyperthyroidism. The method can comprise restricting the amount of iodine intake in the feline. The iodine restriction in the diet can be to a maximum amount equal to or less than about 1 mg/kg of diet, a maximum amount equal to or less than about 0.6 mg/kg of diet, a maximum amount equal to or less than about 0.4 mg/kg of diet or a maximum amount equal to or less than about 0.35 mg/kg of diet on a dry matter basis. Minimum amount of iodine can be an amount to maintain health in the feline and, in particular, an amount equal to or greater than about 0.005 mg/kg or an amount equal to or greater than about 0.01 mg/kg.

In various embodiments, the present invention can also include a packaged feline diet composition containing a reduced amount of iodine. The iodine restriction in the diet can be to a maximum amount equal to or less than about 1 mg/kg of diet, a maximum amount equal to or less than about 0.6 mg/kg of diet, a maximum amount equal to or less than about 0.4 mg/kg of diet or a maximum amount equal to or less than about 0.35 mg/kg of diet on a dry matter basis. Minimum amount of iodine can be an amount to maintain health in the feline and, in particular, an amount equal to or greater than about 0.005 mg/kg or an amount equal to or greater than about 0.01 mg/kg.

In various embodiments, the methods and diet compositions can contain from about 10% to about 50% protein, from about 15% to about 45% protein, from about 20% to about 40% protein or from about 25% to about 35% protein on a dry matter basis. The protein can comprise iodine at a concentration of not more than about 0.6 mg/kg crude protein, not more than about 0.4 mg/kg crude protein or not more than about 0.2 mg/kg crude protein. The protein can comprise a vegetable protein such as, for example potato concentrate, soy concentrate, soy protein isolate, soybean meal, corn gluten meal of combinations thereof. Alternatively or additional, the protein comprises an animal protein such as, for example, meat protein isolate, pork lungs, chicken, pork liver, poultry meal, egg or combinations thereof.

The methods and compositions can, in various embodiments, further comprise from about 10 to about 20% fat and from about 5% to about 55% carbohydrate.

DETAILED DESCRIPTION

The present invention, thus, involves diets containing a restricted amount of iodine and methods of feeding such diets to felines having hyperthyroidism to restore thyroid function to a more nearly normal state.

Hyperthyroidism in cats can be diagnosed and assessed as to severity according methods and disease characteristics well known in the art. (see, for example, Peterson et al., in *The cat: diseases and clinical management*, R. G. Sherding, Ed., New York, Churchill Livingstone, 2$^{nd}$ Edition, pp. 1416-1452, 1994; Gerber et al. *Vet Clin North Am Small Anim Pract* 24:541-65, 1994).

The term "iodine," as used herein, refers to the iodine atom without reference to its molecular form. Thus, the term iodine includes without restriction the atom iodine, which may be present in one or more chemical forms, such as iodide, iodate, periodate, erythrosine, and the like.

The abbreviation "T4," as used herein, refers to the iodine-containing amino acid thyroxine, 3,5,3',5'-tetraiodothyronine. The term "free T4" refers to T4 that is not bound to a carrier protein such as thyroid-binding globulin, albumin, prealbumin, and the like.

The abbreviation "T3," as used herein, refers to the iodine-containing amino acid 3,5,3'-triiodothyronine. The term "free T3" refers to T3 that is not bound to a carrier protein such as thyroid-binding globulin, albumin, prealbumin, and the like.

The abbreviation "GSH," as used herein, refers to the tripeptide glutathione.

The abbreviation "GPX," as used herein, refers to the selenium-dependent enzyme glutathione peroxidase.

Concentration of iodine or other mineral elements in foods and feedstuffs can be expressed alternatively on a molar basis (micromoles per kilogram) or on a weight basis (milligrams per kilogram, identical to parts per million, "PPM"). Iodine has a molecular weight of 126.9. Thus a molar concentration of 2.76 micromoles of iodine per kilogram is equal to a weight concentration of 0.35 PPM. Selenium has a molecular weight of 78.96. Thus a molar concentration of 1.25 micromole of selenium per kilogram is equal to a weight concentration of 0.1 mg/kg.

In various embodiments of the present invention, iodine can be present in the diet compositions at a maximum concentration equal to or less than about 1 mg/kg of diet, a maximum concentration equal to or less than about 0.8 mg/kg of diet, a maximum concentration equal to or less than about 0.6 mg/kg of diet, a maximum concentration equal to or less than about 0.4 mg/kg of diet, a maximum concentration equal to or less than about 0.35 mg/kg of diet on a dry matter basis, a maximum concentration equal to or less than about 0.3 mg/kg of diet, a maximum concentration equal to or less than about 0.25 mg/kg of diet, or a maximum concentration of equal to or less than about 0.2 mg/kg diet on a dry matter basis. The minimum concentration of iodine can be an amount sufficient to maintain health in the feline and, in particular, an amount equal to or greater than about 0.005 mg/kg or an amount equal to or greater than about 0.01 mg/kg on a dry matter basis.

Intake in an animal of a nutrient from a food, feedstuff, beverage, or supplement can be expressed as the product of the concentration of the nutrient element in the food, feedstuff, beverage, or supplement and the amount of said food, feedstuff, beverage, or supplement ingested by said animal.

Nutrients can be provided to a feline in the form of cat food. A variety of commonly known cat food products are available to cat owners. The selection of cat and dog food includes, as an example, wet cat foods, semi-moist cat foods, dry cat foods and cat treats. Wet cat food generally has a moisture content greater than about 65%. Semi-moist cat food typically has a moisture content between about 20% and about 65% and may include humectants, potassium sorbate, and other ingredients to prevent microbial growth (bacteria and mold). Dry cat food (kibble) generally has a moisture content below about 10% and its processing typically includes extruding, drying and/or baking in heat. Cat treats typically may be semi-moist, chewable treats; dry treats in any number of forms; chewable bones or baked, extruded or stamped treats; confection treats; or other kinds of treats as is known to one skilled in the art.

Nutrients also may be provided to a feline in a form other than prepared cat food. Thus, for example, Kyle et al. added a vitamin-mineral mixture to a canned cat food (Kyle et al., *New Zealand Veterinary Journal* 42:101-103, 1994). Drinking water or other fluid similarly may be used to provide nutrients to a feline.

Commercial canned cat food products contain varying amounts of iodine and selenium as shown in Tables 1 and 2.

TABLE 1

CANNED CAT FOOD.

| LABEL DESCRIPTION (n = 28) | SELENIUM (mg/kg DM) | IODINE (mg/kg DM) |
|---|---|---|
| SHEBA Gourmet salmon dinner | 0.812 | 1.55 |
| WHISKAS Ground Mealtime | 0.837 | 1.96 |
| WHISKAS Homestyle Chicken & Salmon | 0.863 | 1.18 |
| WHISKAS Ocean Whitefish & Tuna | 1.01 | 2.98 |
| NUTRO Max Cat Chicken & Lamb | 1.28 | 47.87 |
| NUTRO Kitten Chicken & Ocean Fish | 1.34 | 3.24 |
| NUTRO Cat Chicken & Liver Formula | 1.16 | 30.91 |
| FRISKIES Prime Entrée | 1.36 | 4.57 |
| FRISKIES Senior Ocean Whitefish & Rice | 1.78 | 10.59 |
| FANCY FEAST Sliced Beef Feast | 1.50 | 1.30 |
| FANCY FEAST Sardines, Shrimp & Crab | 4.23 | 1.35 |
| FANCY FEAST Ocean Whitefish & Tuna | 2.45 | 5.45 |
| FANCY FEAST Tender Liver & Chicken | 1.84 | 3.08 |
| FANCY FEAST Seafood | 2.09 | 3.27 |
| FANCY FEAST Fish & Shrimp | 3.17 | 1.33 |
| FANCY FEAST Trout | 1.29 | 1.09 |
| FANCY FEAST Tuna & Mackerel | 2.24 | 2.02 |
| HEINZ 9 LIVES Super Supper | 2.38 | 2.47 |
| HEINZ 9 LIVES Ocean Whitefish & Tuna | 1.90 | 5.06 |
| HEINZ 9 LIVES Poached Salmon | 1.60 | 52.27 |
| IAMS Adult Beef Formula | 1.95 | 4.5 |
| IAMS Adult Chicken Formula | 1.32 | 3.18 |
| IAMS Adult Ocean Fish Formula | 2.56 | 5.14 |
| IAMS Adult Salmon Formula | 1.70 | 4.88 |
| BEST CHOICE Ocean Whitefish & Tuna | 1.63 | 2.11 |
| BEST CHOICE Salmon Dinner | 1.66 | 4.38 |
| BEST CHOICE Fisherman's Catch | 2.27 | 4.48 |
| KOZY KITTEN Fish Dinner | 1.32 | 7.07 |
| AVERAGE | 1.77 | 7.83 |

TABLE 2

DRY CAT FOOD.

| LABEL DESCRIPTION (n = 14) | SELENIUM (mg/kg DM) | IODINE (mg/kg DM) |
|---|---|---|
| WHISKAS Original | 0.551 | 1.34 |
| IAMS Kitten Formula | 0.599 | 2.96 |
| IAMS Weight Control Formula | 0.544 | 3.16 |
| IAMS Original Cat Formula | 0.602 | 2.80 |
| EUKANUBA Adult Chicken & Rice | 0.797 | 2.12 |
| PURINA Kitten Chow | 0.973 | 3.05 |
| PURINA Meow Mix Chicken-Turkey-Salmon | 0.636 | 2.39 |
| PURINA Cat Chow Original | 0.729 | 5.94 |
| PURINA O.N.E. Regular | 0.813 | 2.45 |
| NUTRO Max Cat Lite | 0.479 | 3.38 |
| NUTRO Max Cat Chicken-Rice-Lamb | 0.430 | 3.32 |
| FRISKIES Ocean Fish | 0.717 | 1.97 |
| FRISKIES Chef's Blend | 0.720 | 2.17 |
| HEINZ 9 LIVES Tuna & Eggs | 1.01 | 1.79 |
| AVERAGE | 0.69 | 2.77 |

Commercial cat foods generally include ingredients from the following classes: protein from animal and/or plant sources; individual amino acids; fats; carbohydrate sources, vitamins; minerals; and additional functional ingredients such as preservatives, emulsifiers, and the like.

Protein sources for use in cat foods can comprise from 45% to 100% crude protein on a dry matter basis. Twenty-one protein ingredients commonly used in commercial production of cat foods were analyzed for their contents of selenium and iodine. The results were expressed as mg/kg dry matter (DM) and also as mg/kg crude protein (CP) as shown in Table 3 below.

TABLE 3

| | Crude | Selenium | | Iodine | |
| Protein Ingredient | Protein (% DM) | mg/kg DM | mg/kg CP | mg/kg DM | mg/kg CP |
|---|---|---|---|---|---|
| potato concentrate | 75 | 0.08 | 0.11 | 0.084 | 0.11 |
| soy concentrate | 72 | 0.15 | 0.21 | 0.098 | 0.14 |
| soy protein isolate | 91.5 | 0.27 | 0.30 | 0.144 | 0.16 |
| soybean meal | 48.5 | 0.45 | 0.93 | 0.01 | 0.02 |
| corn gluten meal | 64 | 1.25 | 1.95 | 0.02 | 0.03 |
| chicken backs | 75 | 0.41 | 0.55 | 0.02 | 0.03 |
| rice protein isolate | 60 | 0.75 | 1.25 | 0.041 | 0.07 |
| pea protein concentrate | 50 | 1.79 | 3.58 | 0.049 | 0.10 |
| wheat protein conc. | 75 | 1.84 | 2.45 | 0.091 | 0.12 |
| wheat protein isolate | 90 | 2.13 | 2.37 | 0.141 | 0.16 |
| pork liver | 72 | 3.11 | 4.32 | 0.15 | 0.21 |
| beef spleen | 66 | 1.22 | 1.85 | 0.24 | 0.36 |
| beef tongue | 63 | 0.77 | 1.22 | 0.28 | 0.44 |
| pork lung lobes | 75 | 1.71 | 2.28 | 0.29 | 0.39 |
| beef lung | 56 | 0.93 | 1.66 | 0.38 | 0.68 |
| meat protein isolate | 98 | 0.77 | 0.79 | 0.575 | 0.59 |
| deboned turkey | 44.5 | 0.31 | 0.70 | 0.69 | 1.55 |
| Mackerel | 67 | 4.15 | 6.19 | 1.03 | 1.54 |
| Oceanfish | 58 | 1.76 | 3.03 | 1.44 | 2.48 |
| poultry by-product meal | 67 | 0.97 | 1.45 | 2.05 | 3.06 |
| Eggs | 50 | 1.28 | 2.56 | 3.1 | 6.20 |

As shown in the table, potato concentrate and soy isolate contain low selenium and low iodine concentrations.

Protein content in the cat food compositions of the present invention can be in an amount of from about 10%, from about 15%, from about 20%, from about 25%, from about 30%, from about 35% up to about 40%, up to about 45%, up to about 50%, up to about 55%, up to about 60%, up to about 70%, up to about 80%, up to about 90% or greater on a dry matter basis.

Iodine can be present in the protein component at a concentration equal to or less than about 1.0 mg/kg crude protein, a concentration equal to or less than about 0.8 mg/kg crude protein, a concentration equal to or less than about 0.6 mg/kg crude protein, a concentration equal to or less than about 0.4 mg/kg crude protein, a concentration equal to or less than about 0.2 mg/kg crude protein, a concentration equal to or less than about 0.1 mg/kg crude protein, a concentration equal to or less than about 0.05 mg/kg crude protein or a concentration equal to or less than about 0.02 mg/kg.

The protein can be present from animal sources such as meat or meat by-products or from plant sources such as from vegetable protein sources. Animal protein sources can include meat protein isolate, pork lungs, chicken, pork liver, poultry meal, egg and combinations thereof. Vegetable protein sources can include potato concentrate, soy concentrate, soy protein isolate, soybean meal, corn gluten meal and combinations thereof.

Carbohydrate can be supplied from grain ingredients. Such grain ingredients can comprise vegetable materials, typically farinaceous materials, which can supply primarily, dietary digestible carbohydrate and indigestible carbohydrate (fiber) and less than about 15% protein on a dry matter basis. Examples include without limitation brewers rice, yellow corn, corn flour, soybean mill run, rice bran, cellulose, gums, and the like. Typically, carbohydrate can be present in the compositions of the present invention in amounts of from about 5%, from about 10%, from about 15%, from about 20%, from about 25%, from about 30%, up to about 35%, up to about 40%, up to about 45%, up to about 50%, up to about 55%, up to about 60%, up to about 70%, up to about 80%, up to about 90% or greater, on a dry matter basis.

Fats used in cat food include without limitation animal fats and oils, such as choice white grease, chicken fat, and the like; vegetable fats and oils; and fish oils. Fats can be present in the cat food compositions of the present invention in concentrations of from about 5%, from about 10%, from about 15%, up to about 20%, up to about 25%, up to about 30% up to about 35%, up to about 40% or greater on a dry matter basis.

The percentage of ingredients for use in a cat food composition to achieve particular percentages of protein, carbohydrate and fat can be determined by methods well known in the art. For example, one can employ known computer programs using linear programming techniques to design pet food diets with specific characteristics. An example of such a program is the VLCFX ("Visual Least Cost Formulation-eXtended") Product Formulation and Management System provided by Agri-Data Systems, Inc., Phoenix, Ariz.

Individual amino acids can also be included as ingredients in cat food when required to supplement the protein ingredients. Such amino acids that can be added to cat food are known in the art.

Vitamins and minerals may can be included into the cat food compositions of the present invention. Sources of vitamins can include complex natural sources such as brewers yeast, engivita yeast, and the like, and synthetic and purified sources such as choline chloride and the like. Minerals in the cat food compositions of the present invention can include dicalcium phosphate, calcium carbonate, calcium sulfate, potassium chloride, potassium citrate, iodized and non-iodized salt as required to achieve a desired iodine content, and other conventional forms of the mineral nutrients known in the art (see, for example, National Research Council, *Nutrient Requirement of Cats*, Washington, D.C., National Academy of Sciences, page 27, Table 5 footnotes, 1978).

The following examples are further illustrative of the present invention, but it is understood that the invention is not limited thereto.

Example 1

This example illustrates the effect of feeding hyperthyroid cats a low iodine and low selenium diet.

A low iodine, low selenium dry cat food, designated diet 30643, was prepared with the following composition and characteristics: crude protein, 30-34%; fat, 10-20%; carbohydrate, 35-55%; selenium, 0.2 mg/kg on a dry matter basis; iodine, 0.2 mg/kg on a dry matter basis, with grain ingredients comprising 50-55%; vegetable protein (soy concentrate) comprising 30-35%; animal fat comprising 8-10%; and other ingredients comprising 5-6%.

Ten geriatric cats with an average age of 13.5 years and hyperthyroid disease were allotted into two groups based on age and serum total T4 level. One group was fed a control dry cat food containing, per kg of dry matter, 2.5 mg of iodine and 0.6 mg of selenium. The other group was fed diet 30643, containing, per kg of dry matter, 0.2 mg of iodine and 0.2 mg of selenium. The diets were fed for eight weeks. Food intake was measured daily and body weight was measured weekly.

Blood was drawn aseptically every two weeks after overnight removal of food. Blood for complete blood counts and serum for thyroid hormone analyses were analyzed immediately. Blood for other measurements was centrifuged at 5000 g and the serum harvested and frozen and stored at −70° C. until analyzed for serum chemistries and iodine and selenium concentrations.

Serum total T3 and T4 concentrations were measured by radioimmunoassay for use in cats. Serum free T4 concentrations were determined by use of equilibrium dialysis to separate the bound forms from the free forms. Radioimmunoassay was used to measure the concentrations of the free forms in the dialysate.

The assay for estimating free T3 in feline serum used an $^{125}$I-triiodothyronine (T3) derivative that does not bind significantly to the natural binding proteins in serum. In addition, a high affinity antibody was used which binds both the derivative and T3. These two T3 compounds allow for a classical equilibrium radioimmunoassay to be performed without interference from binding proteins and bound T3. The assay antibody was bound to the wall of 12×75 mm polypropylene tubes for simple solid phase separation of bound assay fractions from free fractions. The remainder of the assay was standard radioimmunoassay technology.

Serum and dietary iodine were measured by epithermal instrumental neutron activation analysis (Spate et al., *J Radioanalytical Nuclear Chem* 195: 21-30, 1995).

The results of this feeding trial were as shown in Table 4.

TABLE 4

| Analyte | Diet | Week 0 | Week 8 | Change | Statistical significance | Normal range |
|---|---|---|---|---|---|---|
| Serum total T4, nmol/L | control | 72.8 | 75.3 | +10 | n.s. | 10-55 |
|  | diet 30643 | 74.6 | 47.6 | −27 | P < 0.05 |  |
| Serum free T4, pmol/L | Control | 24.4 | 22.0 | +1 | n.s. | 10-17 |
|  | diet 30643 | 29.6 | 17.6 | −12 | P < 0.05 |  |
| Serum total T3, nmol/L | Control | 1.58 | 1.58 | +0.10 | n.s. | 0.6-1.4 |
|  | diet 30643 | 1.64 | 0.90 | −0.74 | P < 0.05 |  |

TABLE 4-continued

| Analyte | Diet | Week 0 | Week 8 | Change | Statistical significance | Normal range |
|---|---|---|---|---|---|---|
| Serum free T3, pmol/L | Control | 10.52 | 8.18 | −1.60 | n.s. | 1.5-6.0 |
| | diet 30643 | 9.96 | 5.32 | −4.64 | $P < 0.05$ | |
| Serum iodine, mg/L | Control | 0.178 | 0.201 | +0.016 | n.s. | — |
| | diet 30643 | 0.148 | 0.045 | −0.103 | $P < 0.05$ | — |
| Urine iodine, μg/mg creatinine | Control | 1.12 | 0.485 | −0.67 | $P < 0.05$ | — |
| | diet 30643 | 1.09 | 0.034 | −1.06 | $P < 0.05$ | — |
| Serum selenium, mg/L | Control | 0.53 | 0.51 | 0 | n.s. | — |
| | diet 30643 | 0.50 | 0.38 | −0.12 | $P < 0.05$ | — |
| Serum GPX, U/mL | Control | 5.01 | 6.11 | 1.31 | $P < 0.05$ | — |
| | diet 30643 | 4.52 | 4.90 | 0.37 | n.s. | — |

Cats fed diet 30643 showed significant reductions in serum total T3 and T4, to normal levels, whereas the concentrations of these thyroid hormones in cats fed the control diet were unchanged. Free T3 and T4 showed similar statistically significant reductions in the cats fed the diet 30643. Serum selenium and iodine levels decreased in the cats fed the low diet 30643 but were unchanged in the cats fed the control diet. Serum glutathione peroxidase (GPX), an index of selenium nutritional status, was unchanged in the cats fed diet 30643 but increased in the cats fed the control diet. GPX, a selenium-containing enzyme, has important antioxidant functions, so decreased activity of GPX is undesirable. The dietary selenium requirements for growing cats has been shown to be 0.15 mg/kg dry matter (Wedekind et al., *J Anim Physiol Anim Nutr* (Berl) 87: 315-23, 2003). Thus, diet 30643 apparently provided sufficient selenium to maintain GPX activity. Urinary iodine concentrations decreased significantly for cats consuming both diets.

Other observations were significant decreases in serum alanine amino transferase (39%), serum alkaline phosphatase (33%), and serum phosphorus (13%) all of which are consistent with normalization of thyroid function in the cats receiving diet 30643.

Example 2

This example illustrates a factorial study of the effects of feeding hyperthyroid cats a diet low in selenium (Low Se) or a diet low in iodine (Low I), compared to a control diet (High Se & I) with amounts of iodine and selenium approximating the average analytical values for commercial dry cat food described above.

Fifteen geriatric cats with hyperthyroid disease were allotted into three groups and for nine weeks were fed one of three diets comprising dry cat foods of identical compositions except for the contents of iodine and selenium as shown in Table 5.

TABLE 5

| Diet description | Coding | Se (mg/kg DM) | I (mg/kg DM) |
|---|---|---|---|
| Low Selenium, typical iodine | Low Se | 0.30 | 2.49 |
| Low Iodine, typical selenium | Low I | 0.66 | 0.27 |
| Typical Iodine and Selenium | High Se & I | 0.73 | 2.52 |
| Average value of dry cat foods, vide supra | | 0.69 | 2.77 |

The diets comprised a mixture of soy protein isolate concentrate and contained 158 mg/kg dry matter basis of isoflavones. Food intake was measured daily and body weight was measured weekly.

Blood was drawn aseptically after overnight removal of food. Blood for complete blood counts and serum for thyroid hormone analyses were analyzed immediately. Blood for other measurements was centrifuged at 5000 g and the serum harvested and frozen and stored at −70° C. until analyzed for serum chemistries and iodine and selenium concentrations.

Serum and dietary iodine were measured by epithermal instrumental neutron activation analysis (EINAA) at the University of Missouri reactor facility using a boron nitride irradiation capsule as described by Spate et al. Spate V L, Morris J S, Chickos S, Baskett C K, Mason M M, Cheng T P, Reams C L, West C, Furnee C, Willett W, Horn-Ross P. Determination of iodine in human nails via epithermal neutron activation analysis. J Radioanalytical Nuclear Chem 1995; 195: 21-30.

The results of this feeding trial were as shown in Table 6.

TABLE 6

| Analyte | Diet | Week 0 | Week 9 | Change | Statistical significance | Normal range |
|---|---|---|---|---|---|---|
| Serum total T3, nmol/L | Low Se | 70.8 | 90.0 | +19.2 | n.s. | 10-55 |
| | Low I | 79.8 | 46.2 | −33.6 | $P < 0.05$ | |
| | High Se & I | 73.2 | 85.0 | +11.8 | n.s. | |
| Serum total T3, nmol/L | Low Se | 1.42 | 1.70 | +0.28 | n.s. | 0.6-1.4 |
| | Low I | 2.04 | 1.06 | −0.98 | $P < 0.05$ | |
| | High Se & I | 1.54 | 1.76 | +0.22 | n.s. | |
| Serum iodine, mg/L | Low Se | 0.158 | 0.155 | −0.003 | n.s. | — |
| | Low I | 0.148 | 0.049 | −0.099 | $P < 0.05$ | |
| | High Se & I | 0.191 | 0.152 | −0.039 | $P < 0.05$ | |
| Urinary iodine, mcg/mg of creatinine | Low Se | 0.236 | 0.215 | −0.021 | n.s. | — |
| | Low I | 0.245 | 0.047 | −0.198 | $P < 0.05$ | |
| | High Se & I | 0.349 | 0.249 | −0.100 | n.s | |

Feeding cats with hyperthyroidism a low-iodine diet for nine weeks normalized circulating thyroid hormone levels. Feeding a low-selenium diet with a typical iodine content and feeding a high-selenium diet with a typical iodine content had no beneficial effect on circulating thyroid hormone levels in hyperthyroid cats. These results indicate that the selenium content of the diet had little or no effect on the normalization of thyroid function in hyperthyroidism observed in Examples 3 and 4, whereas restricting the iodine intake had a significant normalizing effect on thyroid hormone status.

Example 3

This example illustrates a field trial of the effect of feeding iodine-restricted foods in cats with hyperthyroid disease.

Two feline test diets were formulated to provide iodine at a concentration of 0.35 mg/kg dry matter. One test diet, diet 46836, was manufactured in the form of a dry cat food. The other test diet, diet 50742, was manufactured in the form of a canned cat food. Both the dry cat food and the canned cat food comprised soybean meal. Ten replicates of each manufactured cat food were analyzed for iodine. The iodine content of the dry cat food ranged from 0.27 to 0.60 mg/kg dry matter basis (mean=0.38 mg/kg). The iodine content of the canned cat food ranged from 0.14 to 0.27 mg/kg dry matter basis (mean=0.21 mg/kg).

A multi-center prospective study was conducted to evaluate the effect of these feline test diets in cats with hyperthyroid disease. Measures included thyroid hormone profiles and serum chemistries measured at 0, 2, 4, and 6 weeks. Enrollment criteria were based on elevated total T4 and/or free T4. In the majority of cases, cats also exhibited one or more clinical signs associated with hyperthyroid disease: weight loss, heart murmur/tachycardia, unkempt hair coat, thyroid gland enlargement, increased appetite, vomiting, increased activity, diarrhea, polyuria/polydipsia, aggressiveness, and panting.

Hyperthyroid cats were fed a 50:50 mixture of the canned cat food and dry cat food. In 6 weeks this test diet significantly reduced serum total T4 levels almost to the normal range. Results are shown in Table 7.

TABLE 7

| Metabolite | Week 0 | Week 6 | Change | Significance of change | Normal range |
| --- | --- | --- | --- | --- | --- |
| Serum total T4, nmol/L | 103.0 | 60.1 | −31.5 | P < 0.05 | 10-55 |

The average serum total T4 level decreased substantially in this trial despite the fact that the iodine content of the diet fed to these cats was higher and more variable than that of the diets fed in the earlier trials described in Examples 1 and 2 (Tables 4 and 6). The iodine content of the dry cat food ranged from 0.27 to 0.60 mg/kg dry matter basis (mean=0.38 mg/kg). The iodine content of the canned cat food ranged from 0.14 to 0.27 mg/kg dry matter basis (mean=0.21 mg/lg). The 50:50 mixture of the two cat foods which comprised the diet of these cats was not analyzed directly. However, based on the ranges of iodine content of the individual component cat foods, the iodine content of the diet as fed most likely ranged from about 0.25 mg/kg dry matter basis to about 0.4 mg/kg dry matter basis.

Example 4

This example illustrates the composition of a dry cat food useful in the method of the invention.

The usual method of making pet foods, particularly for dogs and cats, is generally well-known. For dry diets, diet components can be combined in a preconditioner and then fed into an extruder where they are mixed, heated (cooked) and expanded. The extrudate can then be emitted from the extruder and cut using standard knife blades into proper sized particles. Kibbles can then be moved through a dryer to achieve the desired moisture. Kibbles can then be cooled and flavor and other nutrients can be added. Typical diet components include protein ingredients, grain ingredients, various adjuvants such as vitamins, minerals, amino acids and the like, as well as moisture and the like. Other diet components may be applied to the extruded particles.

Wet diets can be prepared in a different manner. Meat, grains and other ingredients can be mixed in a cooker and then deposited in a can. The cans can then be sealed and sent through a retort for sterilization.

In various embodiments of the present invention, the dry cat food comprises one or more protein ingredients of vegetable or animal origin, chosen based on selenium and iodine content. Useful vegetable protein ingredients comprise potato concentrate, soy concentrate, soy protein isolate, soybean meal, and corn gluten meal. Useful protein ingredients of animal origin comprise meat protein isolate, pork lungs, chicken, pork liver, poultry meal, and egg. The protein ingredients, preferably present in amount of 20% to 50% of the total mixture, will provide the bulk of the desired protein content in the final product.

The grain ingredients will include primary farinaceous ingredients, which may be any of the more common grains, such as corn and rice, and their derivatives, including, for example, corn meal and corn flour, as well as sources of dietary fiber, including soybean mill run, cellulose, and the like. Commonly the grain ingredients will be present in amount of 30-65% of the total mass.

The protein ingredients, grain ingredients, vitamins, minerals and amino acids are combined and mixed together. This mixture is processed by heating it above about 212° F. and subjecting it to super-atmospheric pressure in an extruder, and extruding it through an extrusion die into the atmosphere. As the material issues from the die it expands into a porous, expanded product due to the pressure drop across the die and the flashing off of the water as steam. The extrudate is then cut into bite-size kibbles, dried to a moisture content of less than about 10% by weight, optionally coated with fat, optionally dusted with one or more palatability enhancing agents and other functional ingredients known to those skilled in the art, and packaged.

The resulting dry cat food may have the following composition by analysis: moisture, 6.5-7.0%; crude protein, 33.6-35.4%, dry matter basis; iodine, 0.15-0.34 mg/kg, dry matter basis.

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinence of the cited references.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for controlling the serum levels of thyroid hormone T3 and/or T4, the method comprising restricting the amount of iodine intake in a feline from 0.005 mg/kg to less than 1 mg/kg of diet on a dry matter basis.

2. A method according to claim 1, wherein the amount of iodine in the feline is less than 0.35 mg/kg of diet on a dry matter basis.

3. The method according to claim 1, wherein the diet comprises protein at a concentration of from about 10% to about 50% on a dry matter basis.

4. A method according to claim 3, wherein the diet comprises protein at a concentration of from about 20% to about 40% on a dry matter basis.

5. A method according to claim 3, wherein the protein is derived from a protein source that comprises iodine at a concentration of not more than about 0.6 mg/kg crude protein.

6. A method according to claim 5, wherein the protein is derived from a protein source that comprises iodine at a concentration of not more than about 0.2 mg/kg crude protein.

7. A method according to claim 3, wherein the diet further comprises fat at a concentration of from about 10 to about 20% and carbohydrate at a concentration of from about 10% to about 55%.

8. A method according to claim 4, wherein the protein comprises a vegetable protein.

9. A method according to claim 8, wherein the vegetable protein is selected from the group consisting of potato concentrate, soy concentrate, soy protein isolate, soybean meal, corn gluten meal and combinations thereof.

10. A method according to claim 4, wherein the protein comprises an animal protein.

11. A method according to claim 10, wherein the animal protein is selected from the group consisting of meat protein isolate, pork lungs, chicken, pork liver, and combinations thereof.

12. A reduced-iodine packaged feline diet composition comprising iodine in an amount of not greater than about 0.6 mg/kg of diet and vegetable protein in an amount of about 10% to about 60% of the diet on a dry matter basis.

13. A composition according to claim 12 comprising iodine in an amount of not greater than 0.35 mg/kg of diet on a dry matter basis.

14. A composition according to claim 12 comprising iodine in an amount greater than 0.005 mg/kg of diet on a dry matter basis.

15. A composition according to claim 12, comprising protein at a concentration of from about 20% to about 40% on a dry matter basis.

16. A composition according to claim 12, wherein the protein is derived from a protein source that comprises iodine at a concentration of not more than about 0.6 mg/kg crude protein.

17. A composition according to claim 12, wherein the protein is derived from a protein source that comprises iodine at a concentration of not more than about 0.2 mg/kg crude protein.

18. A composition according to claim 12, wherein the composition further comprises fat at a concentration of from about 10% to about 20% and carbohydrate at a concentration of from about 10% to about 55%.

19. A composition according to claim 12, wherein the vegetable protein is selected from the group consisting of potato concentrate, soy concentrate, soy protein isolate, soybean meal, corn gluten meal and combinations thereof.

20. A composition according to claim 12, further comprising animal protein.

21. A composition according to claim 20, wherein the animal protein is selected from the group consisting of meat protein isolate, pork lungs, chicken, pork liver, and combinations thereof.

* * * * *